United States Patent
He et al.

(10) Patent No.: US 12,133,760 B2
(45) Date of Patent: Nov. 5, 2024

(54) ULTRAFAST DOPPLER ULTRASOUND METHOD FOR ESTIMATING BLOOD FLOW VELOCITY THROUGH REPETITIVE COMPOUNDING OF MULTI-ANGLE PLANE WAVES

(71) Applicant: YUNNAN UNIVERSITY, Kunming (CN)

(72) Inventors: Bingbing He, Kunming (CN); Yufeng Zhang, Kunming (CN); Zhiyao Li, Kunming (CN); Hao Li, Kunming (CN); Benxian Yang, Kunming (CN); Zerong Liao, Kunming (CN)

(73) Assignee: YUNNAN UNIVERSITY, Kunming (CN)

( * ) Notice: Subject to any disclaimer, the term of this patent is extended or adjusted under 35 U.S.C. 154(b) by 254 days.

(21) Appl. No.: 17/283,721

(22) PCT Filed: Dec. 2, 2019

(86) PCT No.: PCT/CN2019/122401
§ 371 (c)(1),
(2) Date: Aug. 8, 2022

(87) PCT Pub. No.: WO2021/108953
PCT Pub. Date: Jun. 10, 2021

(65) Prior Publication Data
US 2023/0210490 A1    Jul. 6, 2023

(51) Int. Cl.
*A61B 8/06*    (2006.01)
*A61B 8/08*    (2006.01)

(52) U.S. Cl.
CPC .................. *A61B 8/06* (2013.01); *A61B 8/52* (2013.01); *A61B 8/488* (2013.01)

(58) Field of Classification Search
None
See application file for complete search history.

(56) References Cited

U.S. PATENT DOCUMENTS

2020/0037994 A1* 2/2020 Song .................. G01F 1/712

FOREIGN PATENT DOCUMENTS

CN    103829974 A    6/2014
CN    103845080 A    6/2014
(Continued)

OTHER PUBLICATIONS

Yu et al., "Super-resolution ultrasound imaging method for microvasculature in vivo with a high temporal accuracy," (Sep. 17, 2018), Scientific Reports, vol. 8, Article No. 13918. (Year: 2018).*

(Continued)

*Primary Examiner* — Joel Lamprecht
*Assistant Examiner* — Ashish S Jasani
(74) *Attorney, Agent, or Firm* — Nicholas Mesiti; Heslin Rothenberg Farley & Mesiti P.C.

(57) ABSTRACT

The present disclosure provides an ultrafast Doppler ultrasound method for estimating a blood flow velocity through repetitive compounding of multi-angle plane waves. The method includes: controlling an ultrasonic transducer to cyclically transmit plane waves (101) according to a sequence of deflection angles of $\{0, -\beta, \beta, -\beta\}$; receiving echo signals (102) of the plane waves reflected by an area to be scanned; searching for three consecutive frames of signals with deflection angles in a sequence of $\{0, -\beta, \beta\}$ and $\{\beta, -\beta, 0\}$ in the echo signals to obtain multiple frame groups (103); compounding the three consecutive frames of signals of each frame group to obtain a compounded radio frequency (RF) signal (105); calculating a blood flow velocity (106) according to the compounded RF signal; and performing color coding on the blood flow velocity to (Continued)

generate a two-dimensional (2D) blood flow velocity image (107).

4 Claims, 7 Drawing Sheets

(56) References Cited

FOREIGN PATENT DOCUMENTS

| | | |
|---|---|---|
| CN | 106580369 A | 4/2017 |
| CN | 106725599 A | 5/2017 |
| CN | 110811688 A | 2/2020 |
| EP | 3513735 A1 | 7/2019 |
| KR | 101652727 B1 | 9/2016 |

OTHER PUBLICATIONS

International Search Report for International Patent Application No. PCT/CN2019/122401 (unpublished) (5 pages).
International Search Report for International Patent Application No. PCT/CN2019/122401.

\* cited by examiner

ULTRAFAST DOPPLER ULTRASOUND METHOD FOR ESTIMATING BLOOD FLOW VELOCITY THROUGH REPETITIVE COMPOUNDING OF MULTI-ANGLE PLANE WAVES

CROSS REFERENCE TO RELATED APPLICATIONS

This application is a national stage filing under section 371 of International Application No. PCT/CN2019/122401, filed on Dec. 2, 2019, published on Jun. 10, 2021, as WO 2021/108953, entitled "Ultrafast Doppler Ultrasound Method For Estimating Blood Flow Velocity Through Repetitive Compounding of Multi-Angle Plane Waves," which is incorporated herein by reference in its entirety.

TECHNICAL FIELD

The present disclosure relates to the technical field of ultrasound imaging, in particular to an ultrafast Doppler ultrasound method for estimating a blood flow velocity through repetitive compounding of multi-angle plane waves.

BACKGROUND

In the vascular system, a blood flow velocity profile is used to describe the spatial distribution of blood flow velocities along the radial direction of the lumen. In the flowing process, the blood flows are laminar in the radial direction due to the frictions between blood flows and vessel walls, as well as the blood viscosity. The blood flow velocities on each layer are different, i.e. the fastest in the central layer of the lumen, and gradually slow down toward the vessel walls. In healthy vessels, the blood flow velocity profile is parabolic. In diseased vessels with atherosclerosis, the blood flow velocity profiles are affected by plaque, and thus the parabolic velocity profile is replaced by turbulent flows or even eddy. As the basis of hemodynamics, the blood flow velocity profile is used to calculate hemodynamic parameters such as shear stress, velocity shear rate and wall shear rate.

At present, there are two ultrasound techniques to obtain the blood flow velocity profile: the image velocimetry and Doppler ultrasound. For the image velocimetry, blood speckles are tracked in two consecutive B-mode ultrasound images to obtain the blood flow velocity profile. The processing time of the image velocimetry lags behind the time of the signal acquisition in clinic, Hence, the blood flow velocity profile cannot be presented in real time. For Doppler ultrasound, the blood flow velocities are estimated with the principle of the Doppler shift obtained by the acoustic reflection method. Therefore, it has the advantages of fast processing speed and high measurement accuracy. However, according to the Nyquist sampling theorem, the aliasing will occur and thus cause the failure of the velocity measurement when the pulse repetition frequency is less than the double maximum frequency of the blood flow Doppler signal.

There are two different kinds of Doppler ultrasound techniques to provide the blood flow velocity profile: the Doppler duplex imaging and color flow imaging. The Doppler duplex imaging combines the pulsed Doppler and B-mode ultrasound to simultaneously display the spectrum of Doppler blood flow signals and the structure of surrounding tissues. It has the dual functions measuring distance and velocity. Due to a part of the pulsed repetition frequency is sacrificed for B-mode ultrasound imaging, the detectable maximum velocity of blood flow obtained by this technique is very low. The color flow imaging synchronously displays two-dimensional color blood flow imaging on the B-mode ultrasound image. The flow directions are distinguished with red and blue colors, and the flow velocity is coded by the brightness of the colors. Compared with the pulsed Doppler, the color flow imaging can show the spatial distribution of blood flow velocities more intuitively. However, in order to tradeoff the frame rate of the color flow imaging, the number of ultrasound pulses transmitted at each scanning position is limited, and the sampling time of blood flow Doppler signals is so short that the signal-to-noise ratio is low. In summary, the two Doppler ultrasound techniques are constrained by the pulsed repetition frequency.

In order to solve the above problem, a novel ultrasound imaging technique, namely, ultrafast ultrasound has been developed. The most important developing direction is the plane wave imaging. The plane wave imaging transmits ultrasonic signals by a full aperture through a single transmission, and then acquires all echo signals of the entire imaging area. As same as the pulsed repetition frequency, the frame rate is high to 15,000 frames per second for the imaging depth of 5 cm. However, due to the lack of transmitting focuses, the signal-to-noise ratio of the echo signals is low, and the imaging quality is poor.

Coherent compounding for plane waves is proposed to improve the quality of the plane wave imaging. In this algorithm, multiple plane wave images of the same imaging area are obtained using multiple symmetrical transmitting angles. Note that the active time of all elements in the full aperture is sequentially delayed to realize the inclination of transmitting angles. These multi-angle plane waves are coherently summed to obtain compounded images. Since the coherent compounding algorithm averages many frames of plane wave images, the random noise is effectively reduced, and the signal-to-noise ratio is improved. Moreover, problems such as missing edges of the imaging target can be effectively solved owing to the alteration in transmitting angles.

The sequence of transmitting angles can be set as the alternate or linear change. In the alternate sequence, the duration between two scans with symmetrical angles is shorter. This is more helpful to reduce noise and thus retain useful imaging information. Therefore, the signal-to-noise ratio of the compounded images acquired by the alternate sequence is better than those acquired by the linear sequence. By summing many frames of images to generate a compounded image, the coherent compounding algorithm improves the signal-to-noise ratio. However, it also reduces the pulse repetition frequency, thereby limiting the detectable maximum velocity of blood flow by using the ultrafast Doppler ultrasound.

SUMMARY

An objective of the present disclosure is to provide an ultrafast Doppler ultrasound method for estimating a blood flow velocity through repetitive compounding of multi-angle plane waves. This method increases the pulse repetition frequency by 50%, so as to expand the detectable range of the maximum blood flow velocity of ultrafast Doppler ultrasound.

To achieve the above purpose, the present disclosure provides the following technical solutions.

An ultrafast Doppler ultrasound method for estimating a blood flow velocity through repetitive compounding of multi-angle plane waves includes:

controlling an ultrasonic transducer to cyclically transmit plane waves according to a sequence of deflection angles {0, −β, β, −β} to an area to be scanned;

receiving echo signals of the plane waves reflected by the area to be scanned, where the echo signals are obtained according to a basic cyclic unit of deflection angles arranged in a sequence of {0, −β, β, −β};

searching for three consecutive frames of signals (as a frame group) with deflection angles in a sequence of {0, −β, β} and {β, −β, 0} in the echo signals to obtain multiple frame groups, where, among the multiple frame groups, a last frame signal of a previous frame group of two adjacent frame groups is used as a start frame signal of a next frame group;

compounding the three consecutive frames of signals of each frame group to obtain a compounded radio frequency (RF) signal;

calculating a blood flow velocity according to the compounded RF signal; and performing color coding on the blood flow velocity to generate a two-dimensional (2D) blood flow velocity image.

Optionally, the method further includes: when the ultrasonic transducer is controlled to transmit a plane wave at a deflection angle of 0 to the area to be scanned, activating sequentially all the elements in the full aperture of the ultrasound; and when the ultrasonic transducer is controlled to transmit a plane wave at a deflection angle of −β or β to the area to be scanned, activating sequentially all the elements in the full aperture of the ultrasound based on a delay time calculated by the deflection angle.

Optionally, before compounding the three consecutive frames of signals of each frame group to obtain a compounded RF signal after searching for three consecutive frames of signals (as a frame group) with deflection angles in a sequence of {0, −β, β} and {β, −β, 0} in the echo signals to obtain multiple frame groups, the method further includes:

performing local registration on the three consecutive frames of signals of each frame group.

Optionally, the performing local registration on the three consecutive frames of signals of each frame group specifically includes:

subjecting the three consecutive frames of signals of each frame group to the following operations:

calculating a first offset of the start frame signal relative to an intermediate frame signal;

calculating a second offset of the last frame signal relative to the intermediate frame signal; and performing local registration on the three consecutive frames of signals of each frame group according to the first offset and the second offset.

Optionally, the calculating a blood flow velocity according to the compounded RF signal specifically includes:

extracting a blood flow Doppler signal of each frame of the compounded RF signal from the consecutive multiple frames of the compounded RF signal, to obtain blood flow Doppler signals at different radial positions in a lumen;

performing quadrature demodulation on each of the blood flow Doppler signals to obtain a quadrature component and an in-phase component of each of the blood flow Doppler signals;

calculating a phase shift of each blood flow Doppler signal separately according to the quadrature component and the in-phase component of each of the blood flow Doppler signals;

calculating the blood flow velocity of each blood flow Doppler signal separately according to the phase shift of each blood flow Doppler signal.

According to specific embodiments of the present disclosure, the present disclosure has the following technical effects.

An ultrasonic transducer is controlled to cyclically transmit a sequence of four-angle plane waves with the deflection angles of {0, −β, β, −β}. In the process of coherent compounding, three consecutive RF echo signals with the deflection angles of {0, −β, β} or {β, −β, 0} are used. Among the three RF echo signals, the last RF echo signal is repeatedly used for the next compound. Compared with traditional coherent compounding technologies in which all RF echo signals are compounded only once, the present disclosure increases the pulse repetition frequency by 50%, thereby expanding the detectable range of the maximum blood flow velocity of the ultrafast Doppler ultrasound.

BRIEF DESCRIPTION OF DRAWINGS

In order to describe the technical solutions in the embodiments of the present disclosure or in the prior art more clearly, the accompanying drawings required for the embodiments are briefly described below.

DETAILED DESCRIPTION

The technical solutions in the embodiments of the present disclosure are clearly and completely described below with reference to the accompanying drawings in the embodiments of the present disclosure. Apparently, the described embodiments are merely a part rather than all of the embodiments of the present disclosure.

An objective of the present disclosure is to provide an ultrafast Doppler ultrasound method for estimating a blood flow velocity through repetitive compounding of multi-angle plane waves. This method increases the pulse repetition frequency by 50%, thereby expanding the detectable range of the maximum blood flow velocity of ultrafast Doppler ultrasound.

To make the above objective, features and advantages of the present disclosure clearer and more comprehensible, the present disclosure is further described in detail below with reference to the accompanying drawings and specific embodiments.

Figure 1:
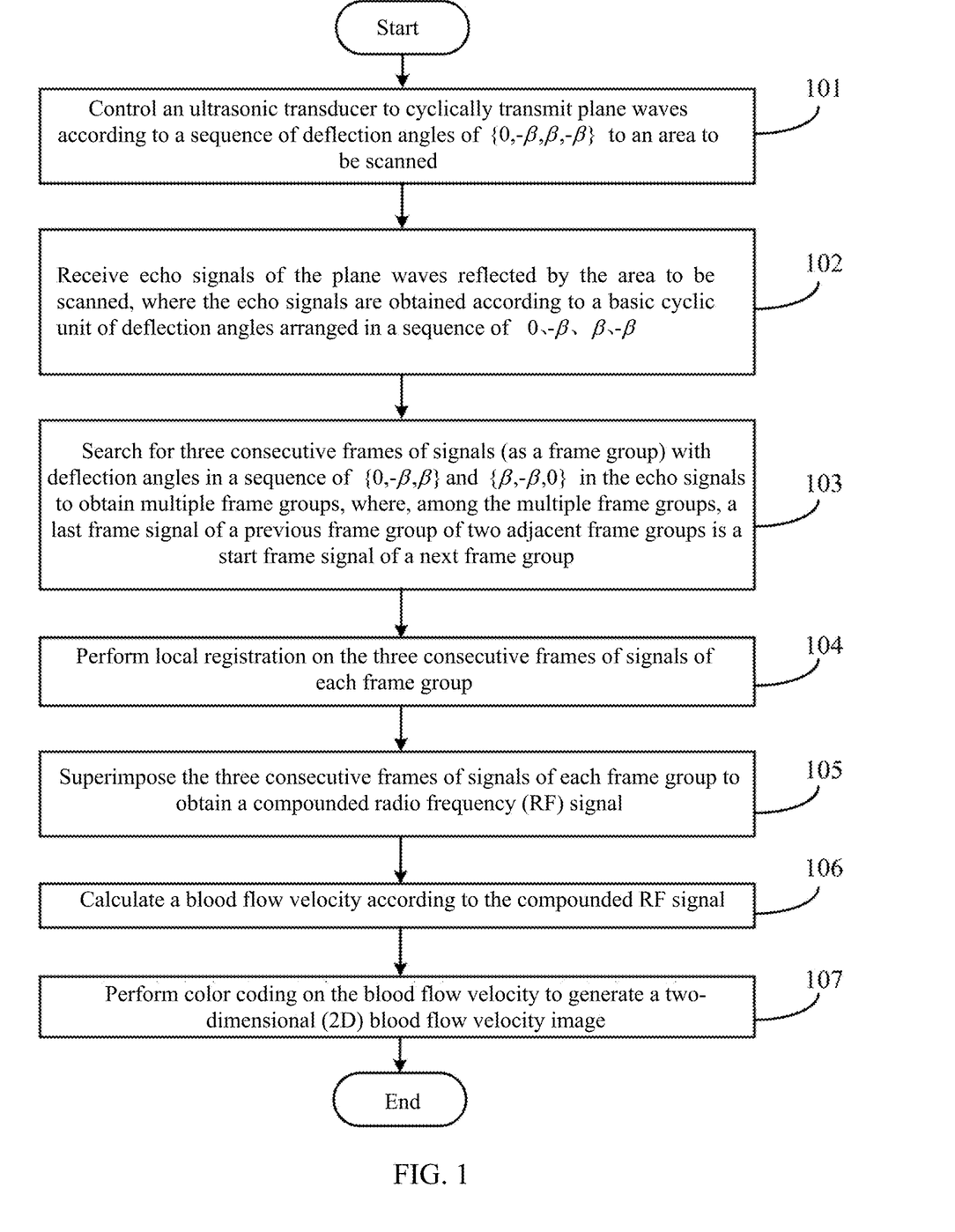
FIG. 1 is a flowchart of an ultrafast Doppler ultrasound method for estimating a blood flow velocity through repetitive compounding of multi-angle plane waves according to the present disclosure.

FIG. 1 is a flowchart of an ultrafast Doppler ultrasound method for estimating, a blood flow velocity through repetitive compounding of multi-angle plane waves according to the present disclosure. As shown in FIG. 1, this method includes:

S101: Control an ultrasonic transducer to cyclically transmit plane waves according to a sequence of deflection angles of $\{0, -\beta, \beta, -\beta\}$ to an area to be scanned.

The specific control method includes: when the ultrasonic transducer is controlled to transmit a plane wave at a deflection angle of 0 to the area to be scanned, activate sequentially all the elements in the full aperture of the ultrasound; and when the ultrasonic transducer is controlled to transmit a plane wave at a deflection angle of $-\beta$ or $\beta$ to the area to be scanned, activate sequentially all the elements in the full aperture of the ultrasound based on a delay time calculated by the deflection angle.

In the ultrasonic transducer with a total of N elements, the delay time of an n-th element is $$t(n) = \frac{(n-1)(w+k)\sin \beta}{c},$$

where $1 \leq n \leq N$; $w$ is a width of the element; $k$ is a distance between two elements; $c$ is a propagation velocity of the ultrasonic waves in an imaging medium.

In this embodiment, a scanning range of the plane waves cyclically transmitted for blood flow scanning is set to X×Z.

S102: Receive echo signals of the plane waves reflected by the area to be scanned, where the echo signals are obtained according to a basic cyclic unit of deflection angles arranged in a sequence of $\{0, -\beta, \beta, -\beta\}$.

Taking point (x,z) in the scanning area as an example, the specific control process of the echo signals of the plane waves received by the ultrasonic transducer is as follows:

The transmission time of the plane wave signal transmitted by the n-th element to point (x,z) in the scanning area is $t_{go}(x,z) = \sqrt{(x-n)^2 + z^2}$. After the signal is reflected by point (x,z) the transmission time of the signal to an n-th element is $t_{back}(x,z) = \sqrt{(n-x)^2 + z^2}$. For point (x,z), the total signal transmission time is $t(x,z) = t_{go}(x,z) + t_{back}(x,z)$.

The signal reflected by all the scattering points in the scanning area is received with a full aperture, and is called channel data (CD).

Based on an ultrasonic delay and sum method, beam synthesis is performed on the CD to generate a radio frequency (RF) echo signal RF. Taking the generation of an RF echo signal RF(x,z) at point (x,z) in the scanning area as an example, there is an equation as follows:

$$RF(x, z) = \int_{x-a}^{x+a} CD(x', t(x, z))dx'$$

In the equation, 2a is a synthetic aperture used in beam synthesis.

Beam synthesis is performed on each frame of CD to obtain RF echo signals of multi-angle plane waves, whose deflection angles are in a sequence of $\{ \ldots, 0, -\beta, \beta, -\beta, 0, -\beta, \beta, -\beta \ldots \}$. In this embodiment, the RF echo signal finally obtained is the echo signal of the plane wave.

S103: Search for three consecutive frames of signals (as a frame group) with deflection angles in a sequence of $\{0, -\beta, \beta\}$ and $\{\beta, -\beta, 0\}$ in the echo signals to obtain multiple frame groups, where, among the multiple frame groups, a last frame signal of a previous frame group of two adjacent frame groups is used as a start frame signal of a next frame group.

S104: Perform local registration on three consecutive frames of signals of each frame group.

The three consecutive frames of signals of each frame group are subject to the following operations:

Calculate a first offset of the start frame signal relative to an intermediate frame signal.

Calculate a second offset of the last frame signal relative to the intermediate frame signal.

Perform local registration on three consecutive frames of signals of each frame group according to the first offset and the second offset.

In this embodiment, the specific control process of local registration is as follows. Three consecutive frames of RF echo signals $\{RF_0, RF_{-\beta}, RF_\beta\}$ or $\{RF_\beta, RF_{-\beta}, RF_0\}$ with the deflection angles of $\{0, -\beta, \beta\}$ or $\{\beta, -\beta, 0\}$ are divided into H×K (horizontally divided into H blocks, vertically divided into K blocks) local RF echo signals. The offsets of the local RF echo signals $RF_0(h,k)$ and $RF_\beta(h,k)$ relative to $RF_{-\beta}(h,k)$ are calculated respectively, and $RF_0(h,k)$, $RF_\beta(h,k)$ and $RF_{-\beta}(h,k)$ are registered according to the offsets, where, $1 \leq h \leq H$, $1 \leq k \leq K$.

S105: Superimpose the three consecutive frames of signals of each frame group to obtain a compounded RF signal.

S106: Calculate a blood flow velocity according to the compounded RF signal.

A blood flow Doppler signal of each frame of the compounded RF signal is extracted from the consecutive multiple frames of the compounded RF signal, to obtain blood flow Doppler signals at different radial positions in a lumen. The blood flow Doppler signals at different radial positions in a k-th frame of compounded RF signal are extracted according to equation $R(k) = RF_k(n,z)$, where $RF_k(n,z)$ represents a z-th sampling point of an n-th line in the k-th frame of compounded RF signal, $1 \leq k \leq K$.

Quadrature demodulation is performed on each blood flow Doppler signal to obtain a quadrature component and an in-phase component of each blood flow Doppler signal. Quadrature demodulation is performed on each blood flow Doppler signal according to equation $R(k) = r(k) + j*I(k)$, where $r(k)$ is the in-phase component of signal $R(k)$ after quadrature demodulation; $I(k)$ is the quadrature component of signal $R(k)$ after quadrature demodulation; $j$ is an imaginary unit.

According to the quadrature component and the in-phase component of each blood flow Doppler signal, the phase shift of each blood flow Doppler signal is calculated separately. An autocorrelation algorithm is used to calculate the phase shift of each blood flow Doppler signal according to equation $$\varphi = \arctan \frac{\sum_{k=2}^{K} I(k)R(k-1) - R(k)I(k-1)}{\sum_{k=2}^{K} R(k)R(k-1) + I(k)I(k-1)},$$

where K indicates that the consecutive multi-frame compounded RF signal has K frames; k represents a k-th frame blood flow Doppler signal; k−1 represents a (k−1)-th frame blood flow Doppler signal; R(k) represents the k-th frame blood flow Doppler signal, I(k) represents the quadrature component of signal R(k) after quadrature demodulation; R(k−1) represents the (k−1)-th frame blood flow Doppler signal; I(k−1) represents the quadrature component of signal R(k−1) after quadrature demodulation.

The blood flow velocity of each blood flow Doppler signal is calculated separately according to the phase shift of each blood flow Doppler signal. The blood flow velocity of each blood flow Doppler signal is calculated according to the Doppler ultrasound equation $$v = \frac{cf_p}{4\pi f_0} \times \varphi,$$

where c represents a velocity of sound; $f_p$ represents a pulse repetition frequency; $f_0$ represents a center frequency of the ultrasonic transducer; φ represents the phase shift of the corresponding blood flow Doppler signal.

S107: Perform color coding on the blood flow velocity to generate a two-dimensional (2D) blood flow velocity image.

Figure 2:
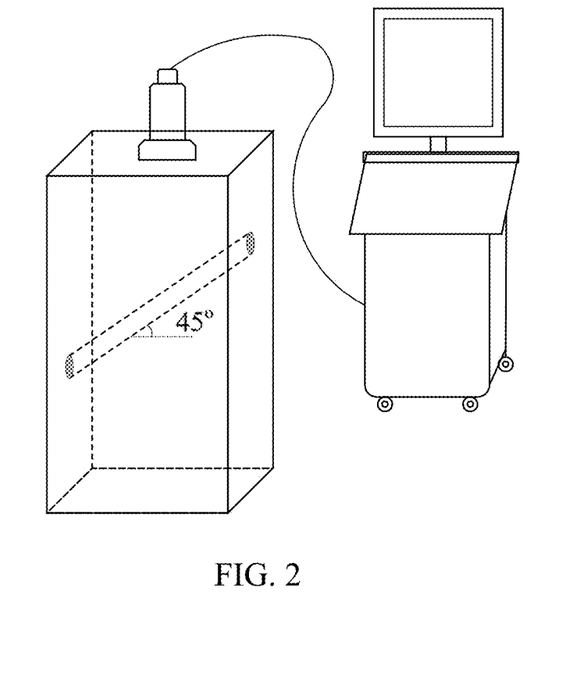
FIG. 2 is a schematic diagram of scanning according to an embodiment of the present disclosure.
Figure 3:
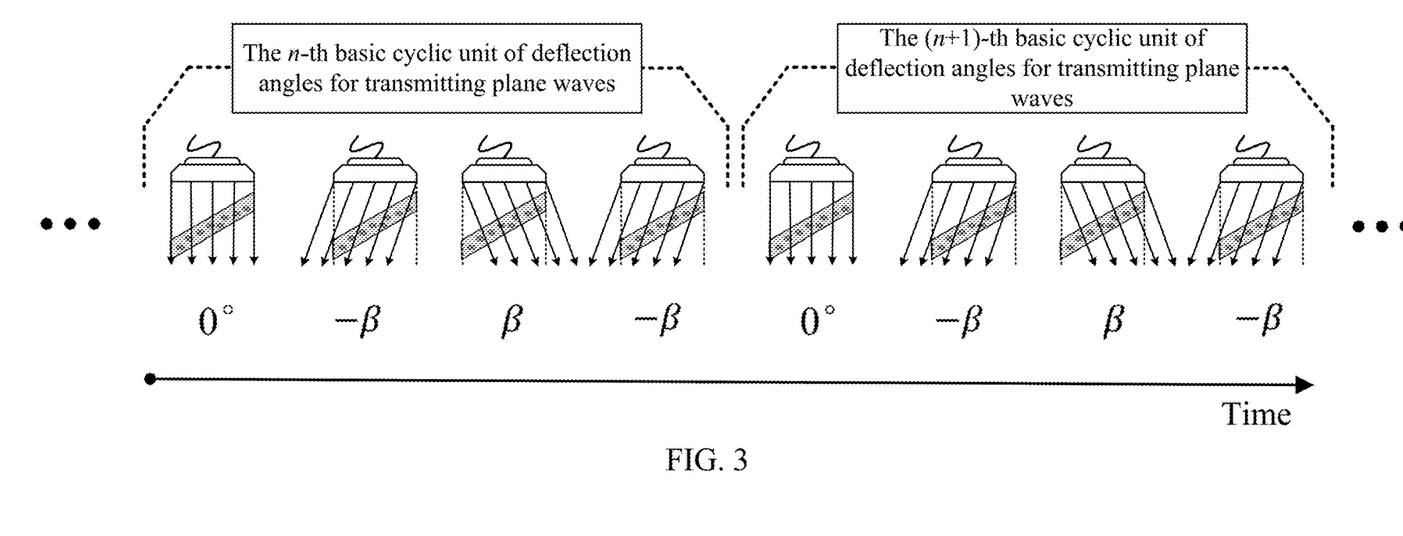
FIG. 3 is a schematic diagram of a time series of cyclically transmitting four-angle plane waves according to an embodiment of the present disclosure.

The technical solution of the present disclosure is described below with reference to a specific embodiment. As shown in FIG. 2, a blood flow model is established. The center maximum speed of the ultrasonic transducer is set to 1.5 m/s, and the deflection angle is set to 45°. The ultrasonic transducer is set to transmit plane waves cyclically at four deflection angles: {0°, −15°, 15°, −15°}. As shown in FIG. 3, according to the set four-deflection transmission cycle, the plane waves are cyclically transmitted for scanning. Based on an ultrasonic delay and sum method, beam synthesis is performed on each frame of CD received by the full aperture of the ultrasonic transducer to obtain an RF echo time series of multi-angle plane waves, whose deflection angles are { . . . , 0°, −15°, 15°, −15°, 0°, −15°, 15°, −15°, . . . }.

Figure 4:
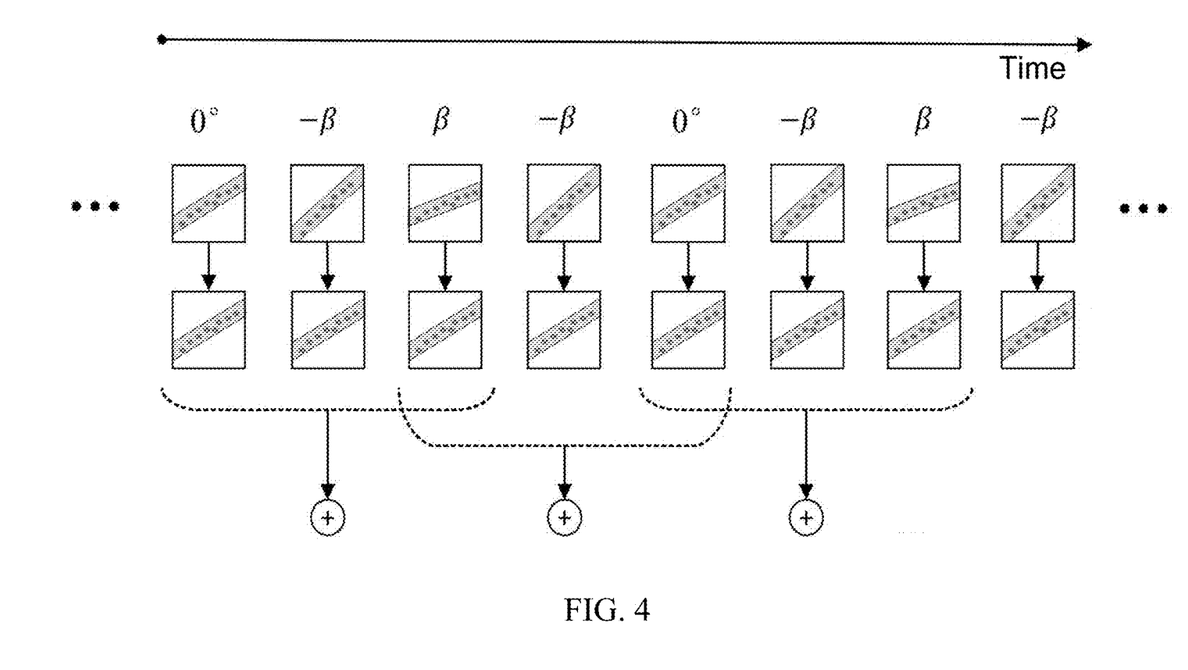
FIG. 4 is a schematic diagram of a time series of a compounded radio frequency (RF) signal based on three-angle plane waves according to an embodiment of the present disclosure.
Figure 5:
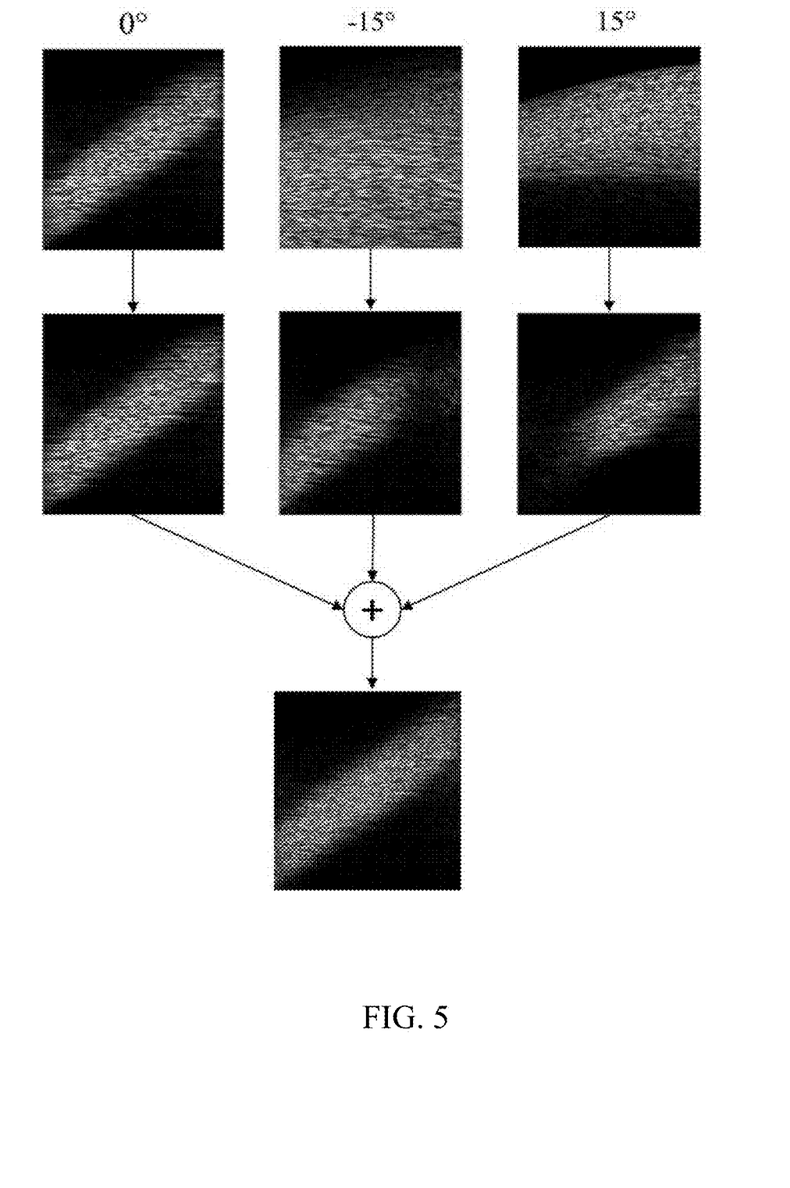
FIG. 5 is a schematic diagram of correction and compound of three-angle plane waves according to an embodiment of the present disclosure.

Local segmentation is performed on three consecutive frames of RF echo signals with the deflection angles of {0°, −15°, 15°} or {15°, −15°, 0°} to obtain local RF echo signals. The offsets of the local RF echo signals of 0° and 15° relative to the local RF echo signal of −15° are calculated, and the local RF echo signals of the three angles are registered according to the offsets. The three frames of RF echo signals after registration are superimposed to generate a frame of compounded RF signal, where the last frame RF echo signal of each compound is repeatedly used for the next compound (as shown in FIGS. 4 and 5).

Blood flow Doppler signals R(k) at different radial positions are extracted from consecutive K=10 frames of compounded RF signals, and quadrature demodulation is performed according to equation R(k)=r(k)+j*I(k), where, 1≤k≤10, r(k) is the in-phase component of signal R(k) after quadrature demodulation; I(k) is the quadrature component of signal R(k) after quadrature demodulation; j is an imaginary unit.

An autocorrelation algorithm is used to calculate the phase shift φ of the blood flow Doppler signal according to equation $$\varphi = \arctan \frac{\sum_{k=2}^{K} I(k)R(k-1) - R(k)I(k-1)}{\sum_{k=2}^{K} R(k)R(k-1) + I(k)I(k-1)},$$

where K indicates that the consecutive multi-frame compounded RF signal has K frames; k represents a k-th frame blood flow Doppler signal; k−1 represents a (k−1)-th frame blood flow Doppler signal; R(k) represents the k-th frame blood flow Doppler signal, I(k) represents the quadrature component of signal R(k) after quadrature demodulation; R(k−1) represents the (k−1)-th frame blood flow Doppler signal; I(k−1) represents the quadrature component of signal R(k−1) after quadrature demodulation.

Figure 6:
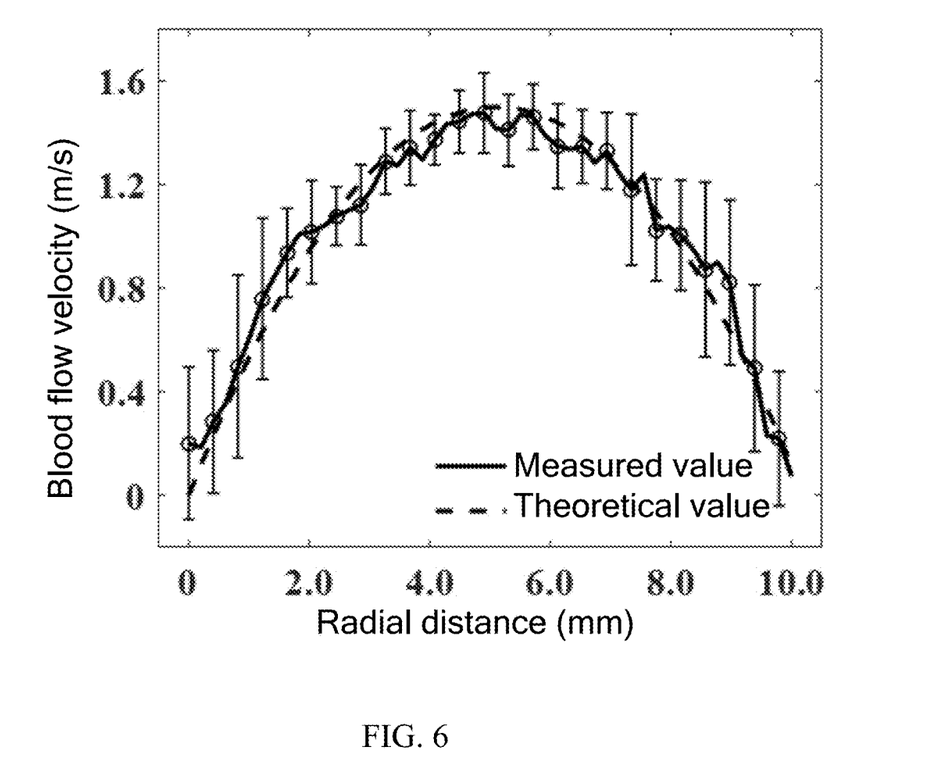
FIG. 6 is a diagram showing the distribution of a radial blood flow velocity measured according to an embodiment of the present disclosure.

As shown in FIG. 6, the blood flow velocity data v of 50 different radial positions are extracted according to the Doppler ultrasound equation $$v = \frac{cf_p}{4\pi f_0} \times \varphi,$$

where c represents a velocity of sound, which is usually 1,540 m/s in human tissues; $f_p$=10000 Hz represents a pulse repetition frequency (equivalent to the frame rate of the compounded RF signal in ultrafast ultrasound); $f_0$=10 MHz represents the center frequency of the ultrasonic transducer; φ represents the phase shift of the corresponding blood flow Doppler signal.

Figure 7:
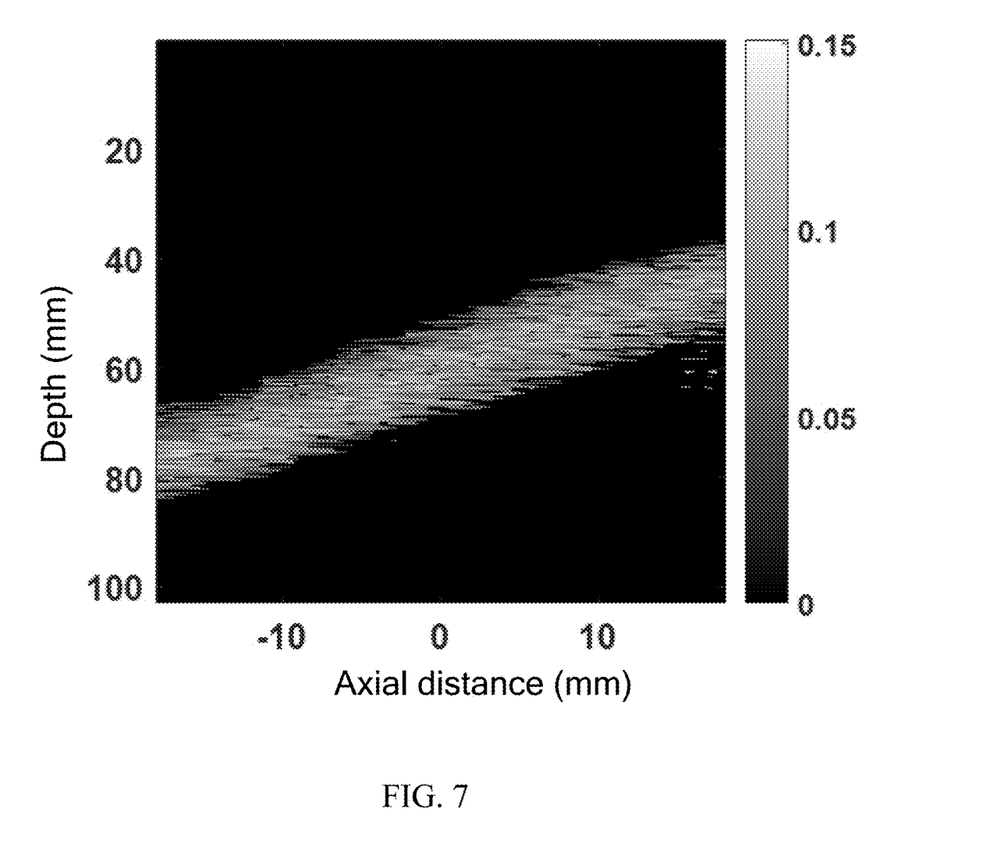
FIG. 7 shows a blood flow velocity image according to an embodiment of the present disclosure.

Finally, color coding is performed based on all blood flow velocity data in the imaging range, to obtain a 2D blood flow speed image in the field of view, as shown in FIG. 7.

In the present disclosure, a sequence of four-angle plane waves with the deflection angles of {0, −β, β, −β} is transmitted cyclically, and in the process of coherent compounding, only three consecutive RF echo signals with the deflection angles of {0, −β, β} or {β, −β, 0} are used. The plane waves of three deflection angles used in each compound compose a polar deflection angle sequence.

The present disclosure introduces local RF echo signal matching. Unlike the traditional method of directly compounding the entire frame of echo signals, the present disclosure performs local matching before the compounding of the three-angle echo signals. Compared with the global registration method (whole frame registration), the present disclosure performs local registration on blood flow RF signals at different radial positions to minimize the motion artifacts of blood flow.

In addition, assuming that the pulse repetition frequency before compounding is $PRF_{single}$, the pulse repetition frequency is $$PRF_{compound} = \frac{PRF_{single}}{3}$$

in the traditional three-angle plane wave coherent compounding method. In the present disclosure, since the last frame of the three-angle plane wave used in each compound is repeated for the next compound, the pulse repetition frequency after repetitive compounding of the three-angle plane waves is $$PRF_{compound} = \frac{PRF_{single}}{3-1} = \frac{PRF_{single}}{2}.$$

Therefore, by using the method of repetitive compounding, the present disclosure increases the pulse repetition frequency by 50%.

Several embodiments are used to illustrate the principles and implementation methods of the present disclosure. The description of the embodiments is intended to help illustrate the method and core principles of the present disclosure. In conclusion, the content of the specification should not be construed as a limitation to the present disclosure.

What is claimed is:

1. An ultrafast Doppler ultrasound method for estimating a blood flow velocity through repetitive compounding of multi-angle plane waves, wherein the method comprises:
   controlling an ultrasonic transducer to cyclically transmit plane waves according to a sequence of deflection angles of $\{0,-\beta,\beta,-\beta\}$ to an area to be scanned;
   receiving echo signals of the plane waves reflected by the area to be scanned, wherein the echo signals are obtained according to a basic cyclic unit of deflection angles arranged in a sequence of $0$、$-\beta$、$\beta$、$-\beta$;
   searching for three consecutive frames of signals (as a frame group) with deflection angles in a sequence of $\{0,-\beta,\beta\}$ and $\{\beta,-\beta,0\}$ in the echo signals to obtain multiple frame groups, wherein, among the multiple frame groups, a last frame signal of a previous frame group of two adjacent frame groups is used as a start frame signal of a next frame group;
   compounding the three consecutive frames of signals of each frame group to obtain a compounded radio frequency (RF) signal;
   calculating a blood flow velocity according to the compounded RF signal; and
   performing color coding on the blood flow velocity to generate a two-dimensional (2D) blood flow velocity image;
   performing local registration on the three consecutive frames of signals of each frame group comprising subjecting the three consecutive frames of signals of each frame group to the following operations:
   calculating a first offset of the start frame signal relative to an intermediate frame signal;
   calculating a second offset of the last frame signal relative to the intermediate frame signal; and
   performing local registration on the three consecutive frames of signals of each frame group according to the first offset and the second offset;
   wherein a specific control process of the local registration is as follows: three consecutive frames of RF echo signals $\{RF_0, RF_{-\beta}, RF_\beta\}$ or $\{RF_\beta, RF_{-\beta}, RF_0\}$ with the deflection angles of $\{0,-\beta,\beta\}$ or $\{\beta,-\beta,0\}$ are divided into H×K (horizontally divided into H blocks, vertically divided into K blocks) local RF echo signals; offsets of
   the local RF echo signals $RF_0((h,k)$ and $RF_\beta(h,k)$ relative to $RF_{-\beta}(h,k)$ are calculated
   respectively, and $RF_0((h,k)$ $RF_\beta(h,k)$ and $RF_{-\beta}(h,k)$ are registered according to the offsets, where, $1 \le h \le H$, $1 \le k \le K$.

2. The ultrafast Doppler ultrasound method for estimating a blood flow velocity through repetitive compounding of multi-angle plane waves according to claim 1, wherein the method further comprises:
   when the ultrasonic transducer is controlled to transmit a plane wave at a deflection angle of 0 to the area to be scanned, activating sequentially all the elements in the full aperture of the ultrasound; and
   when the ultrasonic transducer is controlled to transmit a plane wave at a deflection angle of $-\beta$ or $\beta$ to the area to be scanned, activating sequentially all the elements in the full aperture of the ultrasound based on a delay time calculated by the deflection angle.

3. The ultrafast Doppler ultrasound method for estimating a blood flow velocity through repetitive compounding of multi-angle plane waves according to claim 1, wherein
   before compounding the three consecutive frames of signals of each frame group to obtain a compounded RF signal after searching for three consecutive frames of signals (as a frame group) with deflection angles in a sequence of $\{0,-\beta,\beta\}$ and $\{\beta,-\beta,0\}$ in the echo signals to obtain multiple frame groups, the method further comprises:
   performing local registration on the three consecutive frames of signals of each frame group.

4. The ultrafast Doppler ultrasound method for estimating a blood flow velocity through repetitive compounding of multi-angle plane waves according to claim 1, wherein
   the calculating a blood flow velocity according to the compounded RF signal specifically comprises:
   extracting a blood flow Doppler signal of each frame of the compounded RF signal from the consecutive multiple frames of the compounded RF signal, to obtain blood flow Doppler signals at different radial positions in a lumen;
   performing quadrature demodulation on each of the blood flow Doppler signals to obtain a quadrature component and an in-phase component of each of the blood flow Doppler signals;
   calculating a phase shift of each blood flow Doppler signal separately according to the quadrature component and the in-phase component of each of the blood flow Doppler signals;
   calculating the blood flow velocity of each blood flow Doppler signal separately according to the phase shift of each blood flow Doppler signal.

* * * * *